United States Patent
Seely

(10) Patent No.: US 7,038,595 B2
(45) Date of Patent: May 2, 2006

(54) METHOD AND APPARATUS FOR MULTIPLE PATIENT PARAMETER VARIABILITY ANALYSIS AND DISPLAY

(76) Inventor: Andrew J. E. Seely, 9 Chemin d'Erable, Alcove, Quebec (CA) J0X 1A0

(*) Notice: Subject to any disclaimer, the term of this patent is extended or adjusted under 35 U.S.C. 154(b) by 486 days.

(21) Appl. No.: 10/312,177

(22) PCT Filed: Jul. 3, 2001

(86) PCT No.: PCT/CA01/00979

§ 371 (c)(1), (2), (4) Date: Dec. 24, 2002

(87) PCT Pub. No.: WO02/02006

PCT Pub. Date: Jan. 10, 2002

(65) Prior Publication Data

US 2003/0117296 A1 Jun. 26, 2003

Related U.S. Application Data

(60) Provisional application No. 60/216,374, filed on Jul. 5, 2000.

(51) Int. Cl.
*H04Q 9/00* (2006.01)
(52) U.S. Cl. .............. 340/870.07; 600/300; 128/903; 700/264
(58) Field of Classification Search .......... 340/870.07, 340/870.11, 870.16; 600/300; 607/96
See application file for complete search history.

(56) References Cited

U.S. PATENT DOCUMENTS

| | | | | |
|---|---|---|---|---|
| 5,309,920 A | * | 5/1994 | Gallant et al. | 600/523 |
| 5,438,983 A | | 8/1995 | Falcone | 128/630 |
| 5,579,775 A | * | 12/1996 | Dempsey et al. | 600/483 |
| 5,609,770 A | * | 3/1997 | Zimmerman et al. | 210/739 |
| 5,664,270 A | * | 9/1997 | Bell et al. | 5/600 |
| 5,917,415 A | | 6/1999 | Atlas | 340/575 |
| 6,409,659 B1 | * | 6/2002 | Warner et al. | 600/300 |
| 2002/0192624 A1 | * | 12/2002 | Darby et al. | 434/236 |

OTHER PUBLICATIONS

An Improved Method for Measuring Heart-Rate Variability: Assessment of Cardic Autonomic Function, Biometrics 40,855-861, Sep. 1984, Weinberg et al.

* cited by examiner

*Primary Examiner*—Michael Horabik
*Assistant Examiner*—Sisay Yacob
(74) *Attorney, Agent, or Firm*—Matthew M. Roy; Ogilvy Renault LLP

(57) ABSTRACT

A method and apparatus (100) for providing continuous analysis and display of the variability of multiple patient parameters monitored by multiple bedside monitors (106a–106c) for each patient (102). Each monitor is connected to a patient interface and to a patient data storage unit (115) and a processor (113). Each monitored patient parameter is measured in real-time. Data artifacts are removed, and variability analysis is performed based upon a selected period of observation. Variability analysis yields variability of the patient parameters, which represents a degree to which the patient parameters fluctuate over time, to provide diagnostic information particularly useful in the detection, prevention and treatment of multiple organ dysfunction syndrome (MODS).

19 Claims, 6 Drawing Sheets

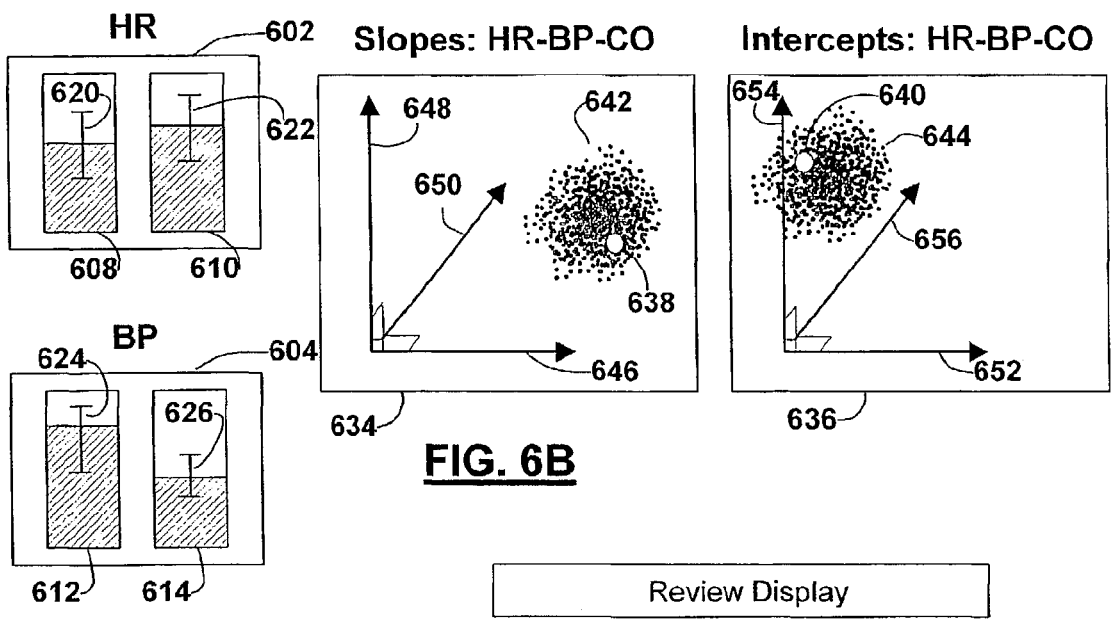
FIG. 6A
FIG. 6B
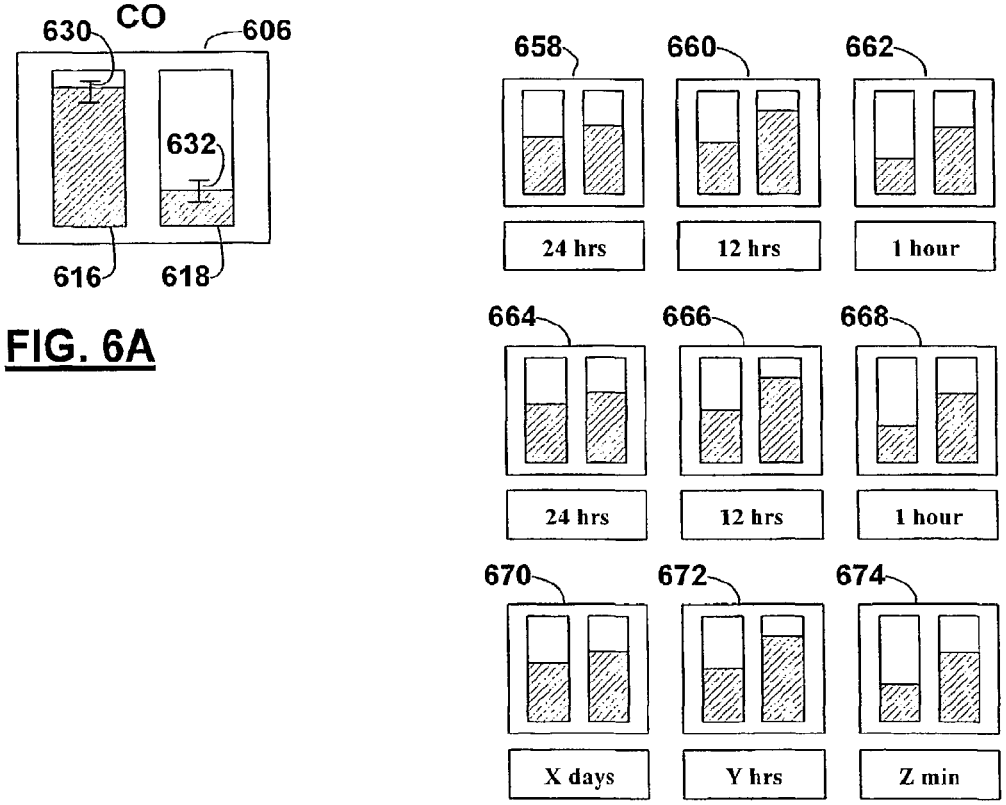
FIG. 6C

METHOD AND APPARATUS FOR MULTIPLE PATIENT PARAMETER VARIABILITY ANALYSIS AND DISPLAY

TECHNICAL FIELD

The present invention relates medical monitoring of patients and more particularly to a method and apparatus for real time monitoring and display of the variability of multiple patient parameters using data collected by an intensive care monitoring unit.

BACKGROUND OF THE INVENTION

Remarkable advances have been made in the care of post-operative and post-injury patients. Because of improvements in the care of acutely injured persons as well as advances in providing organ-specific supportive care, a new class of patients has been created. These patients represent the chronically critically ill. Multiple Organ Dysfunction Syndrome (MODS), defined by having two or more failing organ systems, is the clinical syndrome characteristic of these patients.

MODS is the leading cause of mortality in ICU patients. MODS represents the sequential deterioration of organ function, usually leading to death, occurring in patients who are on the most advanced ICU life support technology possible. These patients require considerable human and hospital resources, including invasive monitoring in an ICU, one-on-one nursing, multiple transfusions, ventilators, dialysis, cardiac assist devices, vasopressors and more. They are the sickest patients in a hospital, and they generally die with MODS.

At present, there is no active treatment that has proven successful for patients with MODS. Over the last three decades, tremendous advances have been made in improving the acute care of critically ill patients by providing organ specific supportive care. However, mortality in patients who survive the initial injury or insult and develop MODS remains unchanged. Extensive basic scientific research has indicated that it is the human host response to a severe physiological insult (e.g. car accident, major surgery, major infection, etc.) that is responsible for the development of progressive organ failure. A dysregulated and overwhelming host response, comprised of many intertwined endocrine, metabolic, neurologic, immune and inflammatory processes, is more complex than, but is analogous to an auto-immune reaction.

Following an exponential growth in the understanding of basic cellular and molecular mechanisms involved in this alteration in host response, numerous attempts at immunomodulation to treat this overwhelming response have been attempted. In over 30 randomized, controlled trials to treat patients with severe infection leading to organ dysfunction, despite compelling supportive laboratory experiments, all attempts at active treatment through immunomodulation have failed. Thus, active treatment of patients with MODS has eluded surgeons and intensivists who care for these patients.

Some of the most important tools used in coronary care units and intensive care units (ICU) are patient monitoring systems. These systems typically use sensors such as electrocardiogram sensors, temperature sensors and blood pressure sensors to measure physiological patient parameters. These patient parameters are then displayed on paper strip charts or video displays at a bedside unit or remotely at a nurse's station. Numerous advances have been made in monitoring systems to provide alarms and improve displays.

Traditional research, has focused on the endocrine, metabolic, cellular and molecular mechanisms involved in the human host response. Current traditional research also tests the efficacy of immunomodulation with clinical trials, where a benefit is evaluated for large cohorts of patients.

Evaluation of variability of patient parameters has only recently come under investigation in medical science, and is generally not used in routine clinical practice. Variability describes the degree to which a parameter fluctuates over time. It is a principal component of the dynamics of a variable, which refers to its pattern of change over time. A parameter may be relatively constant, demonstrating a low degree of variability, or wildly fluctuate with high variability.

The evaluation of heart rate variability has proven to contain valuable information regarding the cardiovascular status of a patient. It can provide accurate and reliable prognostic stratification of mortality risk following myocardial infarction or in patients with heart failure (Kleiger R E et al, American Journal or Cardiology 1987; 59:256 and Odemuyiwa O, et al, American Journal of Cardiology 1991; 68:434). Also, experimental human endotoxin administration will diminish heart rate variability (Godin P J et al, Critical Care Medicine 1996; 24:1117). Thus, diminished heart rate variability is correlated with pathologic alteration of the cardiovascular system.

In addition, evaluation of respiratory impedance variability in healthy controls and patients with asthma revealed increased variability in patients with asthma (Macklem P T, Annals RCPSC 1998, 31:194).

Thus, both increased and decreased variability of individual patient parameters are associated with disease states. The positive clinical significance of the evaluation of these individual variables indicates that the evaluation of multiple patient parameters will provide for clinically useful information. To date, there has been no attempt to provide clinicians with variability analysis of multiple patient parameters simultaneously, nor provide the capability for continuous real-time variability analysis and display.

Further discussion of complex non-linear systems and MODS may also be found elsewhere (A J E Seely, N V Christou, Critical Care Medicine, 28:2193, July 2000).

An example of the state of the art respecting physiological parameter monitoring is U.S. Pat. No. 5,438,983, issued Aug. 8, 1995 to Falcone. Falcone discloses alarm detection using trend vector analysis to provide improved alarm detection. Measured parameters are processed and possibly displayed. A safe zone is determined for these measured parameters and a trend vector is calculated for any measured values falling outside the safe zone. The trend vector can be shown on a display as an arrow indicating a direction and a length that indicates the magnitude of change in the parameter values.

Falcone therefore, gives an indication of the general direction in which a specific parameter is tending when it's values are in a range of values of concern and can provide alarms.

Another example of the state of the art respecting variability monitoring is U.S. Pat. No. 5,917,415, which issued Jun. 29, 1999 to Atlas. The patent teaches a wrist worn device and method for monitoring and alerting the user of increased drowsiness. The device includes sensors for monitoring several physiological parameters of the user, including peripheral pulse rate variability, peripheral vasomotor response, muscle tone, peripheral blood flow and reaction time variability. If the majority of these parameters are indicative of increased drowsiness, the audio-visual alert is provided the user. The sensors are encased in a shock-absorbing unit and wirelessly transmit the sensed data. Atlas monitors a plurality of non-medical parameters to predict a level of drowsiness useful in determining when a driver is no longer alert enough to operate a motor vehicle. The teachings of Atlas cannot be profitably applied to active therapeutic intervention.

In AN ARTICLE ENTITLED AN IMPROVED METHOD FOR MEASURING HEART-RATE VARIABILITY: ASSESSMENT OF CARDIAC AUTONOMIC FUNCTION published in BIOMETRICS 40,855-861, September 1984, Weinberg et al. describe how heart rate oscillates in synchrony with respiration. They proposed an easily computed measure," the static R", which is relatively resistant to the major non-respiratory sources of variation, including premature beats, heart-rate differences among subjects, and slow trends in heart rate over time within subjects. The method can also be used more generally in any context where individuals associate with event processes (for example, with seizures) , when one requires assessment of the extent to which the point process is periodic within a particular known period. The technique is applicable in any context where individual are associated with point processes, such as seizures where it is desirable to assess an extent to which, for a given individuals, the process is periodic with the particular known period, typically a daily or yearly cycle.

Unfortunately, current monitoring systems including that of Falcone, and Weinberg et al. do not provide sufficient prospective evaluation and analysis to identify and quantify changes to the systemic host response, necessary to perform active therapeutic intervention with MODS.

There therefore exists a need for a method and system for evaluating critically ill patients in order to facilitate modulation of the host response.

SUMMARY OF THE INVENTION

It is therefore an object of the invention to provide a method and apparatus for evaluating physiological parameters in order to facilitate active, individualized and effective modulation of a human host response, with the ultimate goal of reducing mortality rates due to MODS.

Another object of the invention is to provide a tool to aid in the evaluation of the overall systemic properties of the human host response in real-time.

The invention therefore provides a method of monitoring variability of a plurality of physiological parameters using data acquired from a plurality of physiological monitoring interfaces, CHARACTERIZED BY:
  collecting data points acquired by each of the plurality of physiological monitoring interfaces for each of the plurality of physiological parameters, respectively;
  removing artifacts from the data points collected from each of the monitoring interfaces;
  continuously computing a measure of variability that represents an estimate of a degree to which a particular physiological parameter fluctuates over time, for each of the plurality of physiological parameters to detect altered emergent properties of a complex non-linear system; and
  continuously displaying the variability for each of the plurality of the physiological parameters.

The invention further provides an apparatus for monitoring variability of a plurality of physiological parameters, CHARACTERIZED BY:
  a processor coupled to a monitor for receiving data points respectively associated with the plurality of physiological parameters and removing artifacts from the received data points, the processor being adapted to continuously compute, for each of the plurality of physiological parameters, a variability representative of an estimate of a degree to which the respective physiological parameters fluctuates over time to detect altered patterns of variability of multiple parameters used to detect altered emergent properties of a complex non-linear system; and
  means for continuously displaying the variability parameter for each of the plurality of physiological parameters.

The paradigm that underlies the invention is one of complex systems, where the focus is on the emergent properties, or the properties of the system, rather than individual components of the system. The focus of the invention is to facilitate individualized care, under an assumption that different persons require completely different types of interventions to modulate a respective host response.

By providing continuous and simultaneous analysis and display of the variability of multiple, accurately measured physiological parameters, pathological alterations in the systemic properties of the host response may be detected. Altered patterns of variability of multiple parameters are used to detect altered emergent properties of a complex non-linear system. Since the host response represents a complex non-linear system, the invention permits alterations in the systemic properties of the host response to be detected.

Physiological parameters capable of variability assessment include any physiological parameter that can be accurately measured. The physiological parameters are ideally measured at regularly recurring intervals, without adverse sequelae for the patient. These include cardiovascular parameters (heart rate, blood pressure, cardiac output, central venous pressure and others), respiratory parameters (airway impedance, respiratory compliance, tidal volume and others), serum biochemistry (glucose, sodium, potassium, insulin level and several others), blood cellular composition (neutrophil count, platelets, hemoglobin level and others). Patterns of variability include the analysis of how several parameters change over time in concert.

This continuous and simultaneous analysis and display of the variability of multiple physiological parameters provides a means for real-time identification and differentiation between physiological and pathological systemic properties of the human host response.

The present invention provides for continuous and simultaneous variability analysis and display of multiple parameters in multiple individuals, in order to:
  determine if an ICU has a physiologic or pathologic pattern of variability on a real-time basis,
  provide prognostic information required to determine a need for therapeutic intervention,
  determine if the response of an individual to a particular intervention is favorable, and
  provide an analysis that serves as a guide to direct further treatment, so that mortality is improved in individuals with MODS.

The present invention provides a method and system that enables continuous data acquisition from multiple physiological parameter monitors to compile data sets; remove artifacts from the data sets, followed by analysis of the variability with the data sets for all monitored parameters, with calculation of variability in physiological parameters utilizing a method of data selection and variability analysis specified by a user who selects specifications from a plurality of pre-defined methods; and continuous display of multiple variability analyses in real time, while permitting user-specified selection of physiological parameters, individuals and choice of variability analysis.

PREFERRED FEATURES OF THE INVENTION

The following illustrates various aspects of the present invention:

A method of monitoring variability of a plurality of physiological parameters using a plurality of physiological monitoring interfaces (104), comprising steps of: collecting data points (402) from each of the plurality of monitoring interfaces (104) for each of the plurality of physiological parameters respectively; continuously computing (408) a variability parameter that represents an estimate of a degree to which a particular physiological parameter fluctuates over time for each of the plurality of physiological parameters; continuously displaying (410) the variability parameter for each of the plurality of physiological parameters.

The method, wherein the step of computing further comprises a step of removing artifacts 406 from the collected data points for each of the plurality of physiological parameters. The method, wherein the step of removing artifacts comprises the steps of using a Pointcaré plot 504, 514, 534 to identify undesirable data points.

The method further comprising a step of selecting a method of computing a variability parameter from a plurality of methods for variability analysis, for each of the plurality of physiological parameters.

The method further comprises a step of selecting which of the plurality of physiological parameters to display.

The method, wherein the step of displaying comprises displaying a correlation between the variability parameters of the plurality of physiological parameters.

The step of displaying, further comprises a step of displaying each of the variability parameters in real time.

The step of collecting data points further comprises a step of collecting data points from a proportional assist ventilator 104a.

An apparatus (100) for monitoring variability of a plurality of physiological parameters, comprising: a processor (107) coupled to a monitoring means, the processor being adapted to continuously compute (110) a variability parameter that represents an estimate of a degree to which a particular physiological parameter measured by the monitoring means fluctuates over time, for each of the plurality of physiological parameters; and a display means (112) for continuously displaying the variability parameter for each of the plurality of physiological parameters.

The apparatus (100) further comprises means (117) for selecting a method of computing a variability parameter from a plurality of predefined methods of variability analysis, for each of the plurality of physiological parameters.

The apparatus (100) further comprises means (117) for selecting a subset of physiological parameters from the plurality of physiological parameters.

The apparatus (100) further comprises means (107) for displaying a correlation between the variability parameters of the plurality of physiological parameters.

The apparatus (100) is further adapted to remove artifacts from the collected data points for each of the plurality of physiological parameters.

The apparatus (100) is further adapted to generate a Pointcaré plot 504, 514, 534 to identify undesirable data points.

The apparatus (100) further comprises means (112) for displaying the variability parameters in real time.

The apparatus (100) further comprises means (112) for displaying the variability parameters of stored data points.

The apparatus (100) further comprises means for measuring data points of respective physiological parameters, for a plurality of individuals.

The display means optionally comprises a multiple physiological parameter variability display (118).

BRIEF DESCRIPTION OF THE DRAWINGS

These and other features, aspects and advantages of the present invention will become better understood with regard to the following description and accompanying drawings wherein:

FIG. 6A illustrates exemplary variability histograms;

FIG. 6B illustrates exemplary plots correlating variability histogram data points for the variability histograms of FIG. 7A; and FIG. 6C illustrates exemplary review displays of variability histograms.

It will be noted that throughout the appended drawings, like features are identified by like reference numerals.

DETAILED DESCRIPTION OF THE PREFERRED EMBODIMENT

The present invention provides a method and apparatus for analyzing and displaying variability of multiple patient parameters related to patients in an Intensive Care Unit (ICU).

Figure 1:
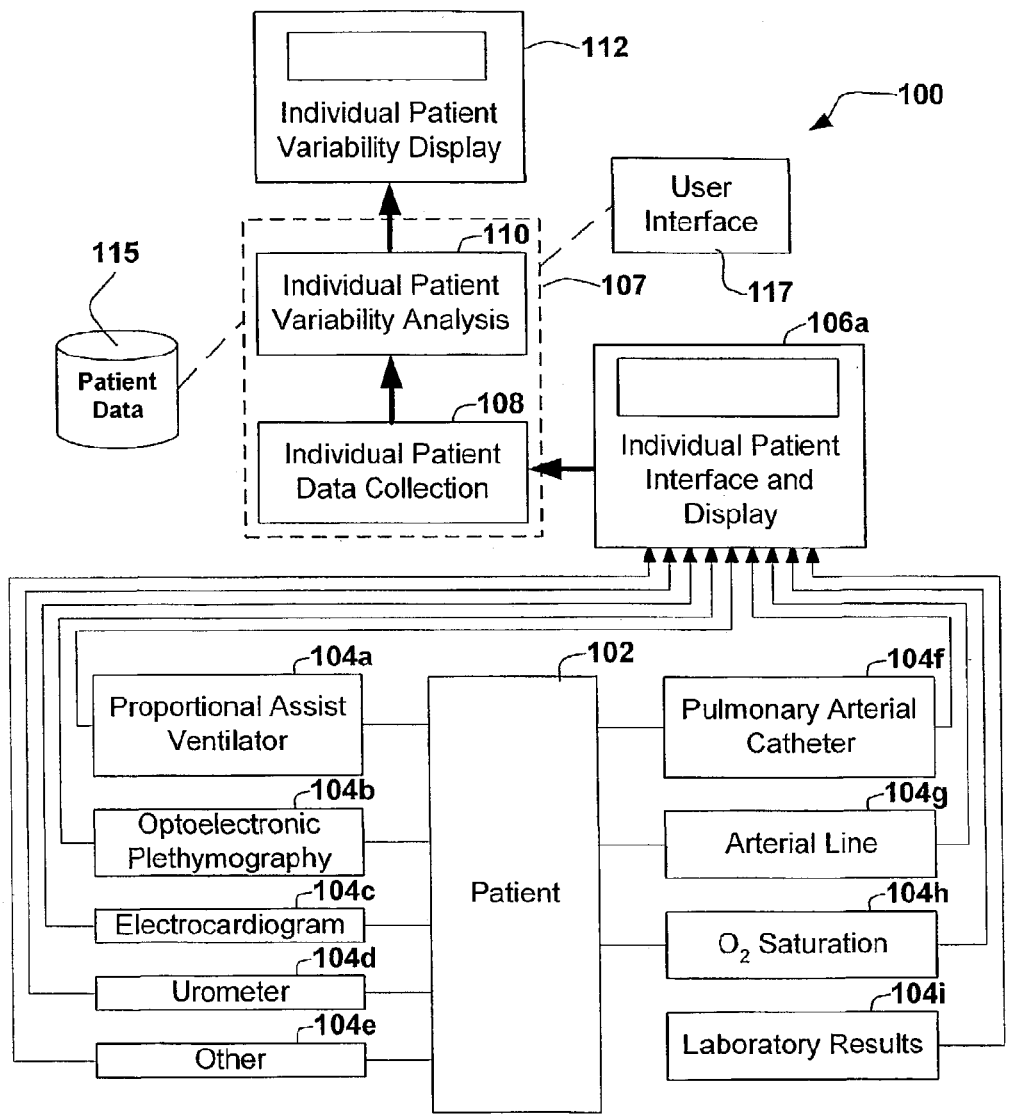
FIG. 1 is a block diagram of an embodiment of the invention for individuals with an individual patient interface.

An organization of various elements of an embodiment of an apparatus 100 in accordance with the present invention is described with reference to FIG. 1. Each patient 102 is connected to one or more patient monitoring interfaces 104 that monitor physiological parameters of the patient. These interfaces include, for example, a proportional assist ventilator 104a, an optoelectronic plethymography 104b, an electrocardiogram 104c, a urometer 104d, a pulmonary arterial catheter 104f, an arterial line 104g, an $O_2$ saturation 104h, and others 104e. External laboratory results can also be included in the monitored parameters. The patient parameters can include any variable that can be accurately measured in real-time. The preferred embodiment of the invention permits data acquisition from each patient 102 via direct connection to an individual patient interface and display 106a of a type well known in the art. The known individual patient interface and display 106a communicates measured values of the patient parameters to an apparatus in accordance with the invention that includes a processor 107 that performs individual patient data collection 108. The collected data is stored, for example, in a patient data store 115. Collected data is then available to a process 110 for performing individual patient variability analysis, the output of which is displayed on an individual patient variability display 112. The process 110 may be selected by a user from among a plurality of variability analysis options using a user interface 117, as will be explained below in more detail.

Figure 1A:
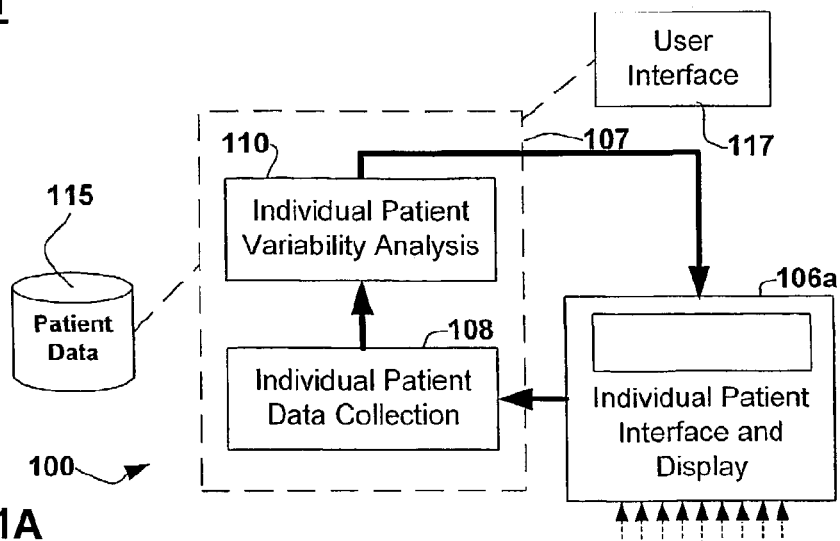
FIG. 1A is a block diagram showing an embodiment of the invention that uses the individual interface display for displaying variability.

In another embodiment of the invention shown in FIG. 1A, the apparatus 100 uses a known individual patient interface and display 106a, having both data input and data output connectors, to provide a display for the variability information.

Figure 2:
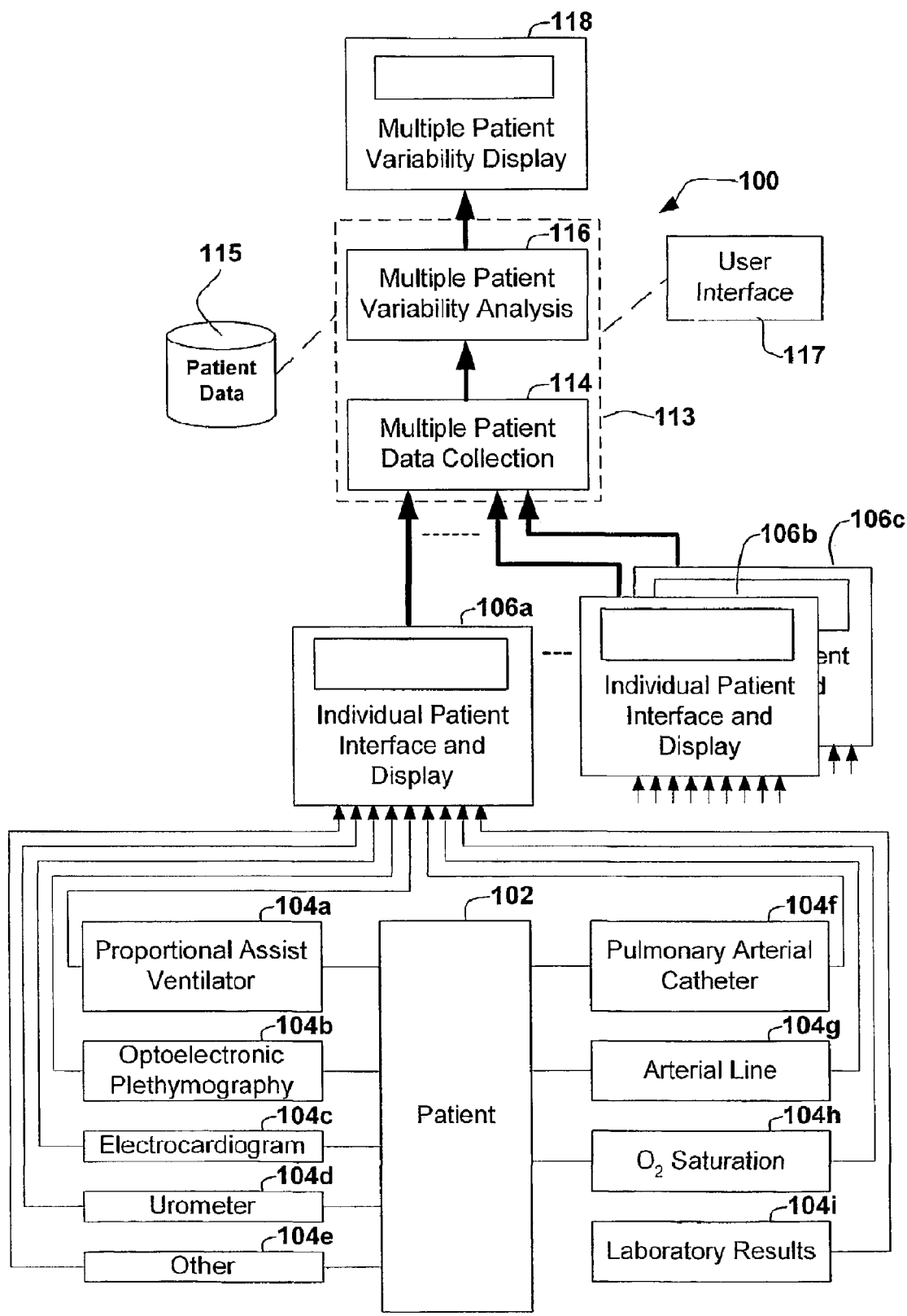
FIG. 2 is a block diagram of an embodiment of the invention having central variability analysis and display for a plurality of individuals.

Another embodiment of the apparatus 100, centralized variability analysis is enabled, for example, at a nurse's station in an ICU, as shown in FIG. 2. The known individual patient interfaces with displays 106a, 106b, 106c communicate data values related to the patient parameters to a central processor 113 for multiple patient data collection 114 in accordance with the invention. The collected data is stored on the patient data store 115. Collected data is then available to a process 116 for performing multiple patient variability analysis, the output of which is displayed on a multiple patient variability display 118. The user interface 117 permits a user to format and control the multiple patient variability display 118. This permits a nurse at a nurse's station to monitor multiple patients in a ward, such as an ICU.

Figure 3:
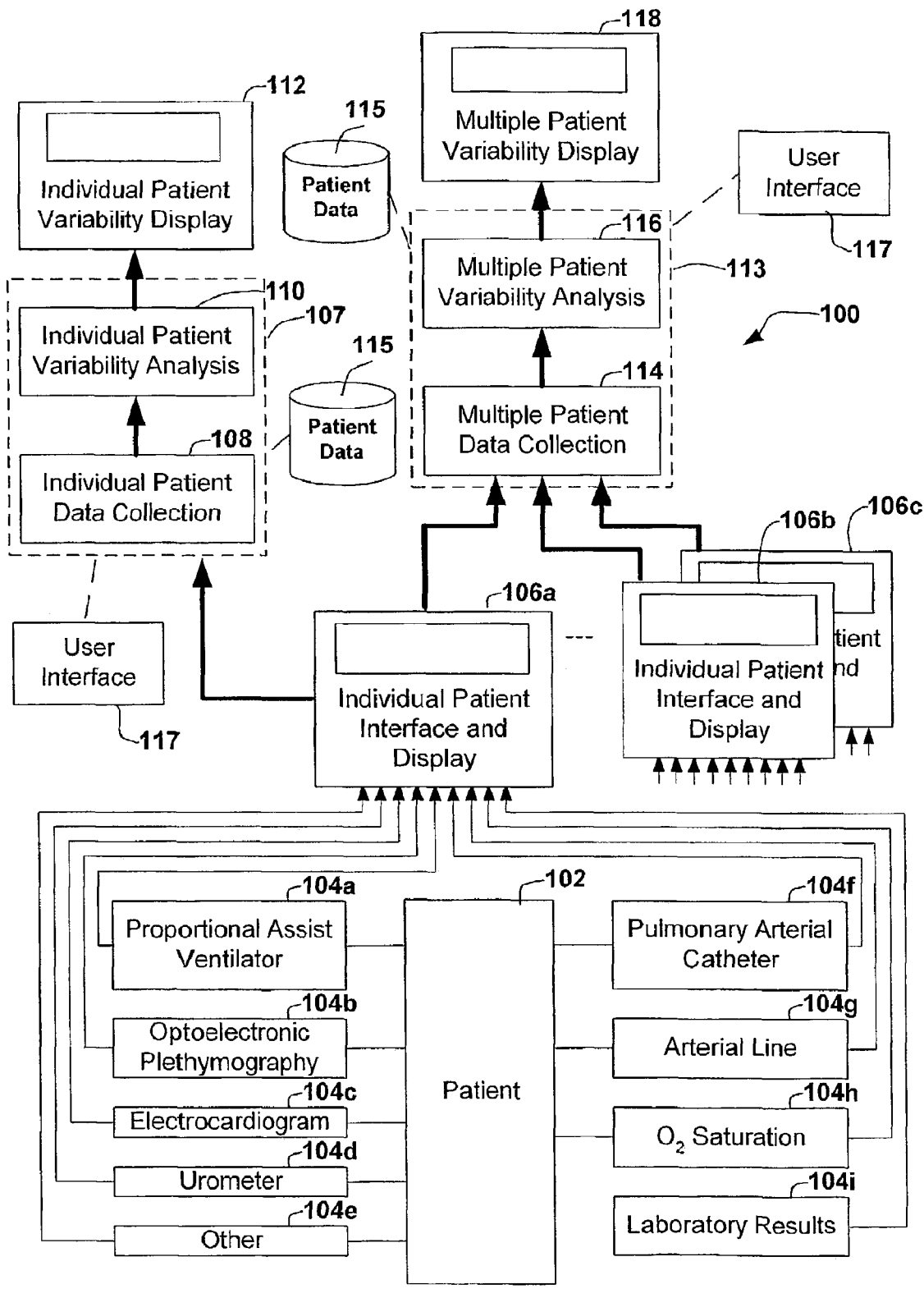
FIG. 3 a block diagram of an embodiment of the invention having individual, as well as central variability analysis and display for a plurality of individuals.

Yet another embodiment of the present invention provides for both individual patient and multiple patient variability analysis and display as shown in FIG. 3. The embodiment shown in FIG. 3 combines the features described above with reference to FIGS. 1 and 2.

A further embodiment of the present invention permits patient monitors 104 (104a–104i) to be directly connected to the apparatus 100 for individual patient data collection 108, and individual patient variability analysis 110.

The method in accordance with the invention includes three main steps: data acquisition; variability analysis; and variability display.

Data Acquisition

Data acquisition involves the sequential recording of consecutive data for each of the patient parameters under investigation. Examples include: continuously recording cardiovascular parameter data; continuously recording respiratory parameter data; and recording other patient parameters at specified time intervals (e.g. glucose levels every 30 minutes).

Patient parameters may be grouped into organ systems to facilitate patient-monitoring and intervention. Table 1 shows patient parameters grouped by organ system.

TABLE 1

| Variability Parameters by Organ System | | | | |
|---|---|---|---|---|
| Cardiovascular | Respiratory | Renal | Liver | CNS |
| Heart Rate | Resp Rate | Urine Output | Arterial pH | EEG |
| Blood Pressure | Arterial $pO_2$ | [Creatinine] | [Glucose] | |

TABLE 1-continued

| Variability Parameters by Organ System | | |
|---|---|---|
| Cardiac Output | Arterial $pCO_2$ | $HCO_3$ |
| CVP | Impedance* | [LDH] |
| $MVO_2$ | Compliance* | |
| SVR | Tidal Volume* | |

| | In-flammatory | Anti-inflammatory | User Specified† | User Specified† |
|---|---|---|---|---|
| Phagocytic | | | | |
| PMN #'s | [TNF-α]‡ | [IL-10]‡ | | |
| Monocyte # | [IL-1] ‡ | [IL-4]‡ | | |
| PMN Apoptosis‡ | [IL-6]‡ | | | |

*Airway impedance and pulmonary compliance are measurable in mechanically ventilated patients by using a Proportional Assist Ventilator
‡Parameters where new technology would aid in safe, readily repeatable measurement. (for example, with very small blood volumes, in a regular, automated fashion)
†The User Specified areas indicate the capacity to enter and organize any additional parameters.

Patient parameters that may be used to evaluate the integrity of the cardiovascular system include any parameter that can be accurately measured at regular intervals that reflects the function of the heart and blood vessels. There are numerous potential variables amenable to variability analysis within the cardiovascular system. This includes heart rate, the first patient parameter that has undergone extensive evaluation of its variability. The interval between heartbeats may be measured precisely by an electrocardiogram, and is known as the R–R' interval. Other parameters that are part of the cardiovascular system and are subject to real-time accurate measurement include blood pressure, cardiac output, central venous pressure, systemic vascular resistance, and others. Blood pressure may be measured with standard arterial in-dwelling catheters or with an automated brachial artery sphygmomanometer. Cardiac output may be continuously measured with transesophageal echocardiography or chest impedance measurement. Central venous pressure may be measured by a catheter placed within the proximal superior vena cava. Other devices may prove to be more reliable or accurate. Important to the selection of monitoring devices will be the lack of artifact, ease of rapid measurement, and patient safety. Nonetheless, any parameter subjected to continuous, accurate measurement, if only for brief periods, can provide data for variability analysis and display.

Parameters representing the integrity of the respiratory system include those indicating adequate oxygenation of the blood and tissue, appropriate ventilation, arterial pH, respiratory rate and respiratory mechanics. The more accurate the measurements of the parameters, the more useful variability analysis becomes.

A situation in which a patient is on a mechanical ventilator deserves special mention, as it will likely be extremely common in the patient population for which the invention is most oriented, chronically critically ill patients. Most current ventilators deliver the same pressure or volume to the patient from breath-to-breath. This limits, but does not completely abrogate the normal variability that is a component of a normal respiratory function. For example, if a patient is on pressure support, despite having the same pressure present to support their ventilation, there is slight variation in the tidal volume from breath to breath. Similarly, pressures may change slightly on volume control ventilation. It may therefore be possible to extract information on respiratory variability using such ventilators. However, other ventilators exist which provide dynamic alteration of both pressure and volume, which improves the significance of the respiratory variability. Specifically, a proportional assist ventilator permits the breath-to-breath alteration and measurement of multiple respiratory parameters, including airway resistance, pulmonary compliance, tidal volume, peak airway pressure. Therefore, a novel use for the proportional assist ventilator is contemplated in which useful data to evaluate respiratory variability is provided. In addition, other novel techniques, such as optoelectronic plethysmography (Aliverti et al, Am J Resp Crit Care Med 2000; 161:1546) may be utilized to evaluate respiratory variability.

Numerous other parameters, as shown in Table 1 (above), may be measured and the resulting data stored for subsequent variability analysis. It is important to note that this invention is not related to the methods or apparatus by which real-time continuous patient data is measured, but rather, is related to the subsequent analysis and display of the variability of multiple patient parameters. It is also important to note that the patient parameters described do not form an exclusive list of patient parameters that can be analyzed using the method and apparatus in accordance with the present invention. Rather, the invention will accommodate any number of patient parameters that are subject to real-time, accurate measurement. Thus, when technology becomes available to measure other patient parameters, related data may be input along with the variables described, in order to provide an even more complete analysis of physiologic or pathologic variability.

Figure 4:
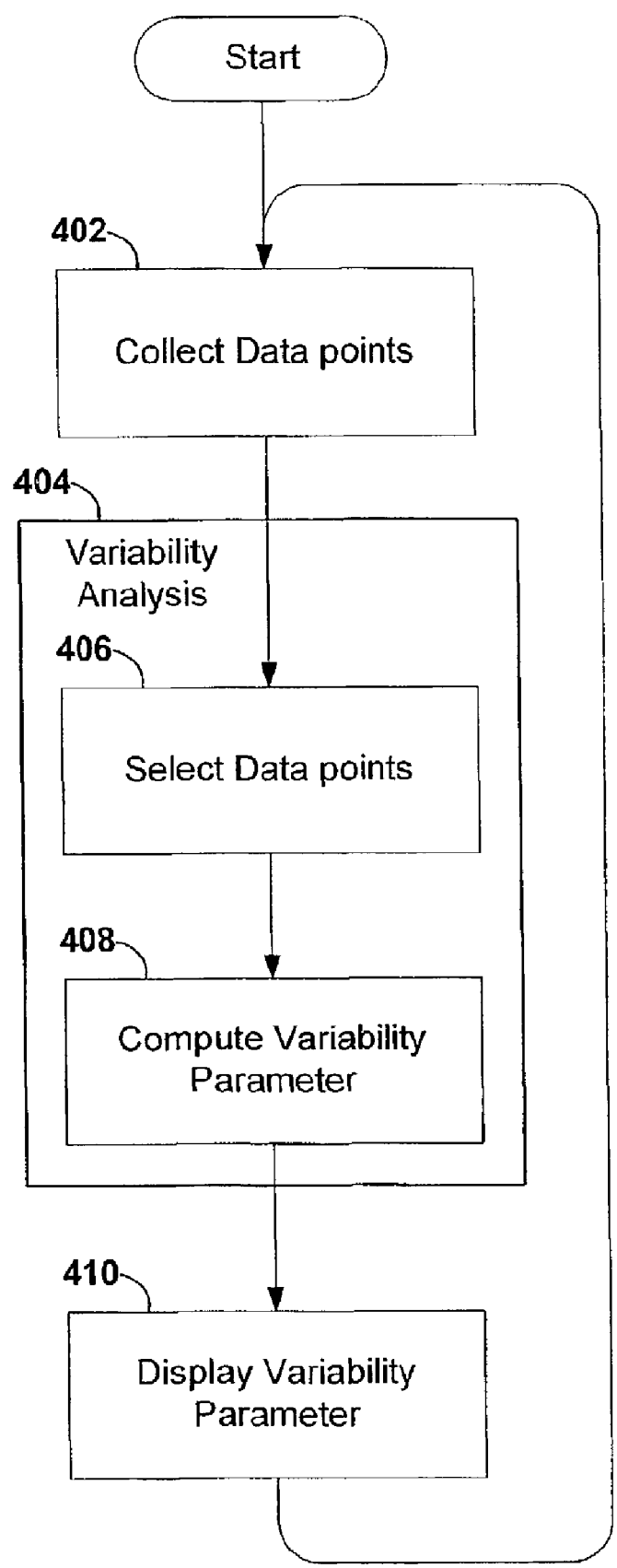
FIG. 4 is a flowchart illustrating the main steps of an embodiment of the method in accordance with the invention.

An embodiment of the method in accordance with the present invention will be described with reference to FIG. 4. The process begins at step 402 where data points are collected for each patient physiologic parameter. Collecting the data involves retrieving or accepting measured data points acquired by patient monitoring interfaces 104, for example, and storing the data points for subsequent analysis on the patient data store 115 (FIGS. 1–3). The data collecting step also includes monitoring a quantity of data collected. Initial analysis may begin after approximately 1000 data points (for example 15 minutes of heart rate measurement) have been collected. For each patient parameter $v_k$, a user, typically an attending physician, may select the number of data points $m_k$ to collect in order to perform the variability analysis. The method computes the time period represented by the selected number of data points. Thereafter, all subsequent calculations are based on the period of time required to collect the $m_k$ data points. Data update preferably occurs as frequently as possible, preferably occurring each cycle. A cycle is defined as the time required to perform the variability analysis for an individual patient parameter. Following the iteration of the next steps, the variability is re-evaluated based on data collected since the last analysis was performed. For example, if a cycle is approximately 1 minute, about 100 data points of heart rate data are collected in each cycle. The collected data displaces the oldest 100 data points previously stored, permitting a new variability analysis to be performed based upon the latest $m_k$ data points. This process enables dynamic evolution of the analysis.

Variability Analysis

Figure 5:
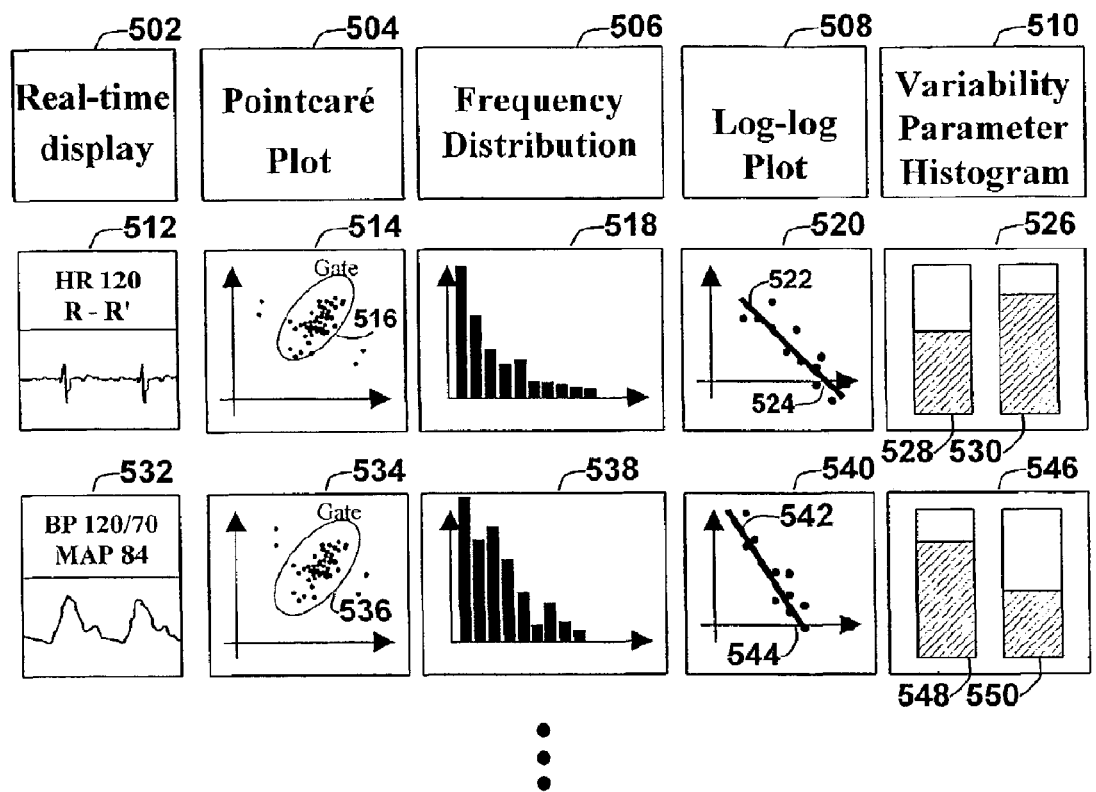
FIG. 5 is a block diagram illustrating exemplary displays for individual variables.

The next step in the process is variability analysis (step 404). The first step in variability analysis is to select data points (step 406). Real data measurement systems often acquire spurious signals that are not relevant to the required analysis. These spurious data points are referred to as artifacts, and it is desirable to remove them in order to make analysis more meaningful. There are many acceptable methods for finding and removing artifacts from sequences of data collected from a wide variety of medical devices. A plurality of methods may be used. In a preferred embodiment, a Pointcaré plot is used. Examples of a Pointcaré plot 514, 534 are shown in FIG. 5. A Pointcaré plot represents differences between consecutive data points. The absolute value of a difference between a data point and the preceding data point $(X_i-X_{i-1})$ is plotted on the x-axis, and the absolute value of a difference between the same data point and the subsequent data point $|X_i-X_{i+1}|$ is plotted on the y-axis. A visual evaluation may be used to eliminate artifact data.

A current data point, and the previous data points may be collected and displayed on the same graph, giving the appearance of a cloud. A user can draw a Gate (illustrated as 516, 536 in FIG. 5) around the data points using tools available through the user interface 117, and a pointing device, for example, thus excluding widely divergent, artifactual data points. The benefit of the Pointcaré plot is that there is a dynamic display of the data in evolution, and there is the ability to dynamically alter the gate. In addition, if too high a percentage of data falls outside the gate, an alarm signal is preferably activated.

Other methods may also be used to remove artifactual data. An absolute value of a parameter may be plotted in succession on a time scale evolution plot, permitting rapid inspection of the data, and removal of artifacts. The original measurement, whether it is an R–R' interval for heart rate, a blood pressure tracing, or whatever, is available to permit the processor 117, or a user to determine whether individual points should be discarded. Thus, storage of data is useful not only for analyzing the data but also reviewing and analyzing previously recorded data. Data artifacts can thus be removed by inspection of the original data measurements.

Several methods may be used to select the data. Different methods may be applied to different data sets, with distinct means of data collection. Therefore a user can select the method by which data artifacts are removed using tools available through the user interface 117. Certain methods of selecting the data are ideal for specific types of data measurement. For example, a Pointcaré Plot is ideally suited for heart rate analysis.

The second step in variability analysis is computing a variability parameter for each of the respective patient parameters (step 408). The variability represents a measure of a degree to which a particular patient parameter fluctuates over time. There are many methods for performing variability analysis. There is no consensus within the scientific literature that a single method of variability analysis is superior for all patient parameters. Heart rate variability (HRV) has been the most extensively studied, and despite considerable research, no method for determining variability has proved consistently better than others. In fact, numerous authors have demonstrated the clinical utility of evaluating HRV using different methods. Different patient parameters may require different methods for evaluating variability, due to differences such as altered statistical properties of the frequency distributions of the respective patient parameters.

In one embodiment of the invention, the apparatus 100 is adapted to display several options for variability analysis to the user, and to advise the user through user interface 117 respecting a suggested method for a particular patient parameter, based upon an algorithm for evaluating the data sets.

The simplest method for computing variability parameters involves the calculation of mean and standard deviation of the frequency distribution of a selected data set. This information can be updated continuously and displayed visually as a graph. Statistical interpretation of the frequency distribution is dependent upon whether the distribution is normal or lognormal. There are standardized means of evaluating whether a distribution is accurately represented by a normal or log-normal curve, which include evaluation of kurtosis and skew. By calculating the kurtosis and skew, the user may be directed towards choosing an appropriate distribution. By evaluating the frequency distribution, the mean and standard deviation would represent the variability parameters for the particular patient parameter under evaluation.

In addition to the mean and standard deviation of the frequency distribution, numerous other methods for computing variability parameters exist. Methods for evaluating variability include spectral and non-spectral analysis, time-frequency analysis, calculation of Lyapunov exponents, approximate entropy, and others (Mansier et al, Cardiovasc Research 1996; 31:371, Glass L, Kaplan D, Med Prog through Tech 1993; 19:115). Preferably the user is presented through the user interface 117 with a choice of several methods, and assisted in selecting a particular method. The results of the variability analysis yield a variability parameter for each patient parameter under evaluation. The variability parameter may then be displayed (step 410), and continuously updated. In each cycle, the updated variability is displayed.

As shown in FIG. 5, the analysis process preferably begins with a real-time display 512, 532 of the respective patient parameters, heart rate 512 and blood pressure 532 in the examples shown. A Pointcaré plot 514, 534 is used, for example, to eliminate data artifacts by establishing a gate 516, 536. A frequency distribution histogram 518, 538 is calculated using the squared difference from the mean of the Pointcaré plot. This method is suitable for data sets that demonstrate 1/f noise. It is a tool for generating a frequency distribution of dispersion from the mean, where all values are positive. The data is plotted in frequency bins, where each bin represents a proportional amount of variation, as measured by the squared difference from the mean. The bins are represented as a histogram, with the frequency on the y-axis, and increasing variation on the x-axis. The bins on the left are normally most full because they represent very common, small variations. The bins on the right, with increasing x-axis, represent large frequency variations, and are usually smaller. In every cycle, the histogram is updated. The Log-log Plot 520, 540 is simply a linear representation of the frequency distribution histogram 518, 538 on a log-log plot of frequency vs. variation. The straight-line distribution of points is characteristic of 1/f noise. The best fit of a straight line through the data points may be derived using standard linear regression analysis, and can also help inform the user respecting the appropriateness of this particular technique. The present invention calculates the slope of the line 522, 542 of the log-log plot and the x-intercept 524, 544. These values can be displayed as pairs of dynamic variability parameter histograms 526, 546. The slope is represented by one histogram 528, 548 and the intercept by another histogram 530, 550.

Variability Display

Variability display represents a means by which a user is able to access the variability of patient parameters computed by the variability analysis method selected by the user.

The preferred mechanism for displaying variability parameters is dynamic variability histograms 526, 546 (FIG. 5) which are represented as columns that increase or decrease in height based on changes in the variability of patient parameters over time.

"Normal" ranges for the variability of each patient parameter for each patient can be determined by analysis over time. Continued research will also provide guidance in this area. Alarms can be set so that if a variability histogram is within the normal range, it is displayed in one color (green, for example). If the value of the histogram rises above or falls below the normal range, it is displayed in a different color (red, for example). The histograms 526, 546 are updated at every cycle.

FIG. 6A illustrates exemplary variability histograms similar to those shown in FIG. 5. Examples are illustrated for heart rate 602, blood pressure 604 and cardiac output 606. Another useful value that can be displayed is a standard deviation of the most recently selected period of variability analysis. This can be super-imposed on the variability histograms as an "I" bar 620, 622, 624, 626, 630, 632.

As described above, the clinical therapeutic potential of this invention is the ability to distinguish pathologic from physiologic systemic properties by monitoring patterns of alterations in the variability of multiple patient parameters. Thus a display can be tailored to best represent the current state of any individual patient with a view to evaluating the physiologic and pathologic properties of individual organ systems, by following the variability of parameters intrinsic to that system.

It is recognized that different organ systems are interrelated and mutually dependent. However, it is beneficial to distinguish between organ systems, because therapeutic intervention is commonly directed towards individual organs. Examples of organ systems include the cardiovascular system, respiratory system, the hematologic system, central nervous system, liver and metabolic system, kidney and waste excretion system.

Thus, the present invention provides flexibility in the display of variability of multiple parameters. The user may select various display options to profile an organ system or a combination of interdependent organ systems. In addition, the user may select any one of:

an individual patient display adapted to display the variability of all monitored parameters for an individual patient;

an individual patient organ specific display, which can display a selected organ system for an individual patient;

a multiple patient display, which can simultaneously display the variability of patient parameters for all patients in a monitored ICU; and a user specified variability display, which can display the variability of user selected patient parameters.

The ability to review changes in variability of patient parameters over time increases the clinical utility of the invention. FIG. 6B illustrates a Variability Review display 634, 636, which is a visual representation of three selected variability parameters 602, 604, 606. One graph 634, represents slope values of the selected parameters 608, 612, 616. The other graph 636, represents the intercept values of the selected parameters 610, 614, 618. In the examples shown in FIG. 6B, for each graph, the heart rate values are plotted on the x-axes 646, 652; blood pressure values are plotted on the y-axes 648, 654; cardiac output values are plotted on the z-axes (depth) 650, 656. Alternatively, the z-axis (depth) can be represented by shades of color. The current variability values are preferably represented by a large dot 638, 640 and the most recent calculated variability values over a set period of time are represented by small dots 642, 644. This permits a visual representation of the data, to enable the user to observe movement of the "cloud of data" over time, as well as any correlation between the selected parameters.

Continued research and user observation helps define desirable physiological patterns of variability. Specific movement of the cloud of data may be desirable and may be stimulated using therapeutic interventions. Thus, a variability review display can be used to facilitate positive intervention.

In addition to the patient and organ specific displays, a display of variability may also be organized into three principal modes: Instantaneous Display, Review Display or Combined Display.

The Instantaneous Display mode provides real-time, continuous display of current variability parameters, the process by which data selection has taken place, and the graphs related to the particular method of variability analysis used for an individual patient parameter. This mode may be used in any of the four user-selected displays (Individual Patient Display, Individual Patient Organ Specific Display, Multiple Patient Display and User Specified Variability Display).

The Review Display (FIG. 6C) permits the user to identify the patterns of alteration in variability parameters over a selected period of time, for selected individual or multiple patient parameters. The Review Display provides the user with a time-compressed, animated display of the variability of selected patient parameters during any selected time period for which data exists. This display mode is similar to a video of the variability over time. This display permits the user to determine the progression of the variability of patient parameters of an individual patient. It also permits the user to determine a response to an intervention, a general progression of illness, or a need for further intervention. Averages of variability in patient parameters, calculated for specific time periods (for example, four hours prior to and four hours following an intervention)can be included in a Review Display.

The Combined Display mode provides a combination of real-time display of current patient parameters, as well as a display of a previous (specified)period of time.

FIG. 6C shows three examples of review display in accordance with the invention. The first row of FIG. 6C shows an example of combined display in which the variability of a patient parameter 24 hours ago (658) is displayed beside the variability of 1 hour ago (660), and the variability in real-time (662).

The second row of FIG. 6C illustrates a review display in which a variability progression is displayed for a patient parameter showing a progression of variability from 48 hours (664), 24 hours (666) and 1 hour (668).

The last row of FIG. 6C shows another review display in which the variability of the patient parameter is displayed at X days (670), Y hours (672) and Z minutes (674).

The invention can be summarized as follows:

A method and apparatus for providing continuous analysis and display of the variability of multiple patient parameters in multiple patients, within an Intensive Care Unit (ICU), for example. In the preferred embodiment, the apparatus is in communication with multiple bedside monitors for each patient that are respectively interconnected with an individual patient interface. The apparatus includes a patient data storage unit and a processor. Each monitored parameter is measured in real-time, and data artifacts are removed. A variability analysis based on a selected period of observation is conducted. Variability analysis yields a variability of the patient parameters, which represent a degree to which a variable fluctuates over time. The user may select any one of several methods for removing artifacts prior to variability analysis. The user may also select from a plurality of methods for performing the variability analysis. The variability analyses may be displayed on a multiple patient display at a central ICU console, as well as individual patient displays at patients' bedsides.

INDUSTRIAL APPLICABILITY

The invention provides a method and apparatus for computing and displaying variability in monitored patient parameters to provide a tool particularly useful in the diagnosis, staging and treatment of MODS, and other pathalogic conditions.

Patient well-being is thereby increased, and unnecessary intervention is avoided. The overall efficiency of the monitoring and reaction process is thereby improved.

The embodiments of the invention described above are intended to be exemplary only. The scope of the invention is therefore intended to be limited solely by the scope of the appended claims.

The invention claimed is:

1. A method of monitoring variability of a plurality of patient parameters using data acquired from a plurality of patient monitoring interfaces, comprising:
    collecting data points acquired by each of the plurality of patient monitoring interfaces for each of the plurality of patient parameters;
    continuously computing a measure of variability of each of the plurality of patient parameters, the measure of variability representing an estimate of a degree and character to which each patient parameter fluctuates over time; and
    continuously displaying a graphic representation of the variability computed for each of the plurality of the patient parameters and continuously displaying a correlation between the variability of the plurality of patient parameters.

2. The method as claimed in claim 1, further comprising a step of selecting for each of the plurality of patient parameters a method of computing the variability from among a plurality of different methods of variability analysis.

3. The method as claimed in claim 1, further comprising a step of selecting the plurality of patient parameters for which the graphic representation of the variability is to be displayed.

4. The method as claimed in claim 1, wherein continuously computing further comprises continuously removing artifacts from the collected data points for each of the plurality of patient parameters.

5. The method as claimed in claim 4, wherein continuously removing the artifacts comprises using a Poincaré plot to identify data points that are artifacts in the collected data points.

6. The method as claimed in claim 1, wherein continuously displaying the graphic representation of the variability further comprises continuously displaying the graphic representations in real time.

7. The method as claimed in claim 1, wherein continuously displaying the graphic representation of the variability further comprises continuously displaying variability histograms.

8. The method as claimed in claim 7, wherein continuously displaying the graphic representations of the variability further comprises continuously displaying the variability histograms in one color if a value of the patient parameter is within a normal range and displaying one or more of the variability histograms in a different color when the value of a corresponding patient parameter rises above or falls below the normal range.

9. The method as claimed in claim 8 further comprising displaying a standard deviation of a most recently selected period of variability analysis as an "I" bar super-imposed on at least one of the variability histograms.

10. The method as claimed in claim 1 further comprising providing a review display mode that presents a time-compressed, animated display of the variability of selected patient parameters during any selected time period for which data exists.

11. The method as claimed in claim 1 further comprising providing a combined display mode that provides a combination of real-time display of current patient parameters, and a display of the variability of patient parameters during a specified previous period of time.

12. A system for monitoring variability of a plurality of patient parameters, comprising:
   a processor coupled to a plurality of patient monitors for receiving data points respectively associated with the plurality of patient parameters, the processor continuously computing, for each of the plurality of patient parameters, a variability of each patient parameter representative of an estimate of a degree and character to which the respective patient parameters fluctuate over time; and
   a console for continuously displaying a graphic representation of the variability computed for each of the plurality of the patient parameters and continuously displaying a correlation between the variability of the plurality of patient parameters.

13. The system as claimed in claim 12, further comprising a user interface for permitting a user to select a method of computing each variability parameter from among a plurality of methods of variability analysis.

14. The system as claimed in claim 12 further comprising a user interface for permitting a user to select a subset of patient parameters from the monitored plurality of patient parameters for which the variability is to be continuously displayed on the console.

15. The system as claimed in claim 12, wherein the processor removes artifacts from the collected data points for each of the plurality of patient parameters.

16. The system as claimed in claim 15, wherein the processor generates a Poincaré plot to identify the artifacts to be removed from the collected data points.

17. The system as claimed in claim 12, wherein the console displays the variability parameter for each of the plurality of patient parameters as a plurality of dynamic variability histograms.

18. A patient monitoring system, comprising:
   a processor that performs continuous data acquisition from multiple patient parameter monitors to compile respective data sets, the processor removing artifacts from the data sets, and computing a variability using the data sets of each monitored patient parameter;
   a user interface that permits a user to select a method of data selection and variability analysis from among a plurality of pre-defined methods for selecting data and computing the variability of each of the patient parameters; and
   a console for continuously displaying a graphic representation of the variability computed for each of the plurality of the patient parameters and continuously displaying a correlation between the variability of the plurality of patient parameters.

19. The system as claimed in claim 18 wherein the processor comprises a central processor for multiple patient data collection and the system further comprises;
   a patient data store for storing patient data collected from multiple patient parameter monitors for each of a plurality of patients; and
   a console for displaying a multiple patient variability display.

* * * * *